(12) United States Patent
Kankan et al.

(10) Patent No.: US 7,550,593 B2
(45) Date of Patent: Jun. 23, 2009

(54) PROCESS FOR THE PREPARATION OF FINASTERIDE FORM I

(75) Inventors: Rajendra Narayanrao Kankan, Maharashtra (IN); Dharmaraj Ramachandra Rao, Maharashtra (IN)

(73) Assignee: Cipla Limited, Mumbai (IN)

( * ) Notice: Subject to any disclaimer, the term of this patent is extended or adjusted under 35 U.S.C. 154(b) by 65 days.

(21) Appl. No.: 10/563,138

(22) PCT Filed: Jul. 5, 2004

(86) PCT No.: PCT/GB2004/002906

§ 371 (c)(1),
(2), (4) Date: May 1, 2006

(87) PCT Pub. No.: WO2005/003149

PCT Pub. Date: Jan. 13, 2005

(65) Prior Publication Data

US 2007/0021455 A1    Jan. 25, 2007

(30) Foreign Application Priority Data

Jul. 3, 2003    (IN)    ................ 676/MUM/2003

(51) Int. Cl.
*C07D 221/18*    (2006.01)
*C07D 221/04*    (2006.01)

(52) U.S. Cl. ........................................ 546/77; 546/61

(58) Field of Classification Search .................. 514/284; 546/77, 61
See application file for complete search history.

(56) References Cited

U.S. PATENT DOCUMENTS

| 4,760,071 A | 7/1988 | Rasmusson et al. |
| 5,652,365 A | 7/1997 | McCauley et al. |
| 5,670,643 A | 9/1997 | Davis et al. |

FOREIGN PATENT DOCUMENTS

| EP | 0599376 | 6/1994 |
| WO | 0132683 | 5/2001 |
| WO | 2004 039828 | 5/2004 |

OTHER PUBLICATIONS

US2002/0042425, Abstract, Inventor Gormley, Glenn J; Transdermal treatment with 5-alpha reductase inhibitors.

*Primary Examiner*—Charanjit S Aulakh
(74) *Attorney, Agent, or Firm*—Conley Rose, P.C.; Rodney B. Carroll

(57) ABSTRACT

A process of preparing finasteride Form (I), which process comprises dissolving finasteride in a solvent, replacing the solvent partially or substantially completely with a nonsolvent and thereafter isolating finasteride Form (I). There is also provided finasteride Form (I) prepared in accordance with the present invention, and the therapeutic use thereof in the inhibition of 5-alpha reductase, and pharmaceutical compositions containing the same.

8 Claims, No Drawings

PROCESS FOR THE PREPARATION OF FINASTERIDE FORM I

This application is a 35 USC § 371 U.S. National Stage Application of International Application No. PCT/GB2004/002906, filed on Jul. 5, 2004, claiming the priority of Indian Application No. 676/MUM/2003, filed Jul. 3, 2003, the entire disclosures of which are incorporated herein by reference in their entireties.

The present invention is concerned with an improved process for the preparation of finasteride Form I, finasteride Form I prepared by the process of the present invention, pharmaceutical compositions including the same, therapeutic uses thereof and methods of treatment employing the same.

5-alpha reductase is an enzyme associated with the nuclear membrane and it is found in high concentrations in the human male reproductive tissues, skin and liver. 5-alpha reductase catalyses the conversion of testosterone to dihydrotestosterone (DHT). Two isoenzymes (type I and II) of 5-alpha reductase have been identified in the human tissue. The type I isoenzyme is found in scalp skin, while the type II isoenzyme is found in the prostrate. Type I 5-alpha reductase is responsible for approximately one third of circulating DHT and type II 5-alpha reductase is responsible for about the remaining two thirds of the circulating DHT. In men with male pattern hair loss (androgenetic alopecia), the balding scalp contains miniaturized hair follicles and increased amounts of DHT compared to hairy scalp.

Finasteride, 17β-(N-t-butyl carbamoyl)-4-aza-5-alpha-androst-1-ene-3-one, is a potent inhibitor of the type II 5-alpha reductase. Finasteride selectively blocks the production of dihydrotestosterone by competitive inhibition of 5-alpha reductase, resulting in significant decreases in serum and tissue DHT concentrations. Finasteride produces a rapid reduction in serum DHT concentration, reaching 65% suppression within 24 hours of oral dosing with a 1 mg tablet.

Various prior art disclosures provide for different processes for producing and isolating finasteride Form I, by using different organic solvents, or a mixture of protic and aprotic solvents.

U.S. Pat. No. 4,760,071 discloses a process for the preparation of 17β-(N-monosubstituted carbamoyl)-4-aza-5-alpha-androst-1-ene-3-one, pharmaceutical compositions useful in inhibiting testosterone 5-alpha reductase, and methods of treating hyperandrogenic conditions using the same, particularly benign prostatic hyperplasia.

U.S. Pat. No. 5,652,365 discloses a process for producing finasteride Form I, which comprises crystallizing a solution of finasteride in a water immiscible organic solvent, optionally comprising water, so as to obtain solvated and non-solvated finasteride in solution. In accordance with this process, the amount of organic solvent and water in the solution is sufficient to cause the solubility of the non-solvated form of finasteride to be exceeded. The non-solvated form of finasteride is less soluble than any other form of finasteride in the organic solvent and water solution. The process further comprises recovering the resultant solid phase and removing the solvent. The organic solvent is ethyl acetate or isopropyl acetate and the amount of water in the solvent mixture is below 4 mg/ml.

U.S. Pat. No. 5,886,184, and corresponding European Patent 0599376B, discloses a process for producing finasteride which comprises reacting the magnesium halide salt of 17β-carboalkoxy-4-aza-5-alpha-androst-1-ene-3-one with t-butylamino magnesium halide, present in at least a 2:1 molar ratio to the ester, formed from t-butyl amine and an aliphatic magnesium halide at ambient temperature in an inert organic solvent under an inert atmosphere followed by heating and recovering the product finasteride as polymorphic crystalline Forms I and II.

US Patent Application 20020042425A1 discloses an invention that involves a method of treating and/or reversing androgenic alopecia and promoting hair growth, and methods of treating acne vulgaris, seborrhoea, and female hirsutism, by administering to a patient in need of such treatment a 5-alpha reductase II inhibitor, such as finasteride, in a dosage amount of less than 5 mg/day. The invention further provides a process to finasteride, employing a solvent such as glacial acetic acid.

U.S. Pat. No. 5,670,643 discloses a process of preparing finasteride by reacting an acid chloride with t-butylamine in an aprotic solvent, e.g. pyridine, toluene, methylene chloride, dimethylformamide or acetonitrile, in the presence of a base, e.g. pyridine, diisopropylethylamine, dimethylaminopyridine, or triethylamine, at a temperature in the range of about 20-60° C. Salts such as LiCl and LiBr can be used to facilitate this reaction. The resulting compound can be purified by known techniques, such as chromatography and crystallization.

There are several disadvantages associated with the known methods for obtaining polymorphic Form I of finasteride. In the known methods, finasteride Form I is obtained from solvents, or mixtures of solvents, such as tetrahydrofuran, glacial acetic acid, ethyl acetate, toluene and/or isopropyl acetate. Typically, one of the principal disadvantages in the prior art processes is that during the drying step the solvents are difficult to remove from the crystals and pure crystals are not therefore obtained by carrying out the processes known in the art. A further disadvantage associated with known processes is that they are generally unsuitable for use on an industrial scale.

There is a need, therefore, for improved processes for the industrial preparation of finasteride Form I, wherein the process is suitable for large scale manufacture and does not employ too many controls, the residue of solvents in the crystals is very low and the resulting crystals are free flowing and suitable for converting to dosage forms directly or after micronisation.

The present invention alleviates the problems associated with the prior art preparation of finasteride Form I and according to the present invention, therefore, there is provided a process of preparing finasteride Form I, which process comprises dissolving finasteride in a solvent, replacing the solvent partially or substantially completely with a non-solvent and thereafter isolating finasteride Form I.

In a first preferred embodiment of a process according to the present invention, replacing the solvent with the non-solvent comprises distilling off the solvent followed by addition of the non-solvent, whereby a process according to the present invention comprises the steps of: (i) dissolving finasteride in a solvent to form a solution; (ii) distilling off the solvent from the solution obtained in step (i); (iii) adding a non-solvent to the product of step (ii); and (iv) isolating finasteride Form I.

Suitably, the finasteride is initially dissolved in a solvent such as methanol or dichloromethane, and the dissolution may be carried out at a temperature in the range of ambient to reflux, as appropriate. The resulting solution of finasteride in the solvent may optionally be clarified using decolourising agents.

A non-solvent as employed in a process according to the present invention typically comprises a poor solvent for finasteride and as such, when added to a solution or slurry comprising finasteride, results in precipitation thereof. Suitably the non-solvent is water. Alternatively, the non-solvent is an organic solvent in which the solubility of finasteride in not more than about 5% w/v, or 1 in 20 at the boiling point thereof. Suitably, the organic non-solvent may be selected from straight chain or branched alkanes, such as hexane, heptane or octane, or aromatic solvents, such as toluene or xylene, or esters such as isobutyl acetate or isopropyl acetate. Typically, in a process according to the present invention distillation is continued following addition of the non-solvent.

Suitably a process according to the present invention further comprises stirring a precipitated product obtained further to addition of the non-solvent for a period sufficient to obtain finasteride Form I, for example for a period sufficient to transform finasteride to finasteride Form I. A preferred process according to the present invention can, therefore, comprises dissolving finasteride in a solvent, replacing the solvent partially or substantially completely with a non-solvent, stirring a precipitated product obtained further to addition of the non-solvent and thereafter isolating finasteride Form I.

The finasteride starting material employed in a process according to the present invention comprises finasteride as prepared by processes known in the art, for example as described in the basic finasteride patent U.S. Pat. No. 4,760,071 substantially as hereinbefore described.

The present invention further provides finasteride Form I prepared by a process according to the present invention substantially as hereinbefore described. Finasteride Form I as provided by the present invention comprises substantially pure finasteride Form I, and is substantially free of associated impurities. More specifically, there is provided finasteride Form I having a purity of at least about 99.6% w/w, more preferably at least about 99.7% w/w and in certain embodiments at least about 99.8% w/w.

The present invention further provides pharmaceutical compositions comprising a therapeutically effective amount of finasteride Form I as provided according to the present invention, together with one or more pharmaceutically acceptable carriers, diluents or excipients therefore.

By "pharmaceutically acceptable" it is meant that the carrier, diluent or excipient must be compatible with finasteride Form I as provided according to the present invention, and not be deleterious to a recipient thereof.

The pharmaceutical compositions or medicaments are prepared in a manner well known in the pharmaceutical art. The carrier, diluent or excipient may be a solid, semi-solid, or liquid material, which can serve as a vehicle or medium for the active ingredient. Suitable carriers, diluents or excipients are well known in the art. Pharmaceutical compositions according to the present invention may be adapted for oral or parenteral use and may be administered to the patient in the form of tablets, capsules, suppositories, solutions, suspensions or the like.

Preferably compositions as provided by the present invention comprise oral dosage forms selected from the group consisting of tablets, capsules (each including timed release and sustained release formulations), pills, powders, granules, elixirs, solutions, suspensions, syrups and emulsions. Suitably a pharmaceutical composition according to the present invention comprises isolated substantially pure polymorphic Form I of finasteride. A composition according to the present invention is suitably substantially equivalent to 1 mg to 500 mg of finasteride.

In still a further preferred embodiment, the present invention provides a process for preparing finasteride tablets for oral administration, which tablets are film-coated tablets containing 1 mg or 5 mg of finasteride. Conventional methods are employed in mixing finasteride Form I with inactive ingredients, such as intra-granular ingredients (for example, lactose monohydrate, sodium starch glycolate and starch), binder (for example, starch, lactose monohydrate and purified water), extra-granular ingredients (for example, colloidal silicon dioxide, sodium benzoate, sodium starch glycolate and magnesium stearate), and coating the tablet by using coating agents such as opadry 04F50702 blue and purified water.

Finasteride Form I as provided by the present invention has therapeutic utility as a 5-alpha reductase inhibitor, for example in the treatment of acne vulgaris, seborrhea, female hirsutism, androgenic alopecia which includes female and male pattern baldness, and in particular benign prostatic hyperplasia.

In addition, the present invention further provides a method of inhibiting 5-alpha reductase in a patient in need thereof comprising administering to said patient an effective inhibitory amount of finasteride Form I as provided according to the present invention.

The present invention also provides use of finasteride Form I as provided according to the present invention in the manufacture of a medicament for inhibiting 5-alpha reductase.

The present invention is illustrated below with reference to the following Examples.

EXAMPLES

Example 1

Dichloromethane (150 L) and finasteride (11 kg) were charged to a reactor and stirred to dissolve. Dichloromethane was distilled out and water (120 L) was added and the distillation was continued until the vapour temperature reached about 80° C. The contents were cooled to ambient and stirred for 24-30 hours and the product was filtered and washed with water and dried under vacuum to obtain finasteride Form I having purity of about 99.7%.

Example 2

Methanol (170 L) and finasteride (10 kg) were charged to a reactor, and neutral alumina (1 kg) and activated charcoal (1 kg) were added and stirred for 15 minutes at a temperature of 25-35° C. and filtered. The filtrate was transferred to another reactor and methanol was distilled out until a thick slurry was obtained Toluene (70 L) was added and the distillation was continued until the vapour temperature reached about 110° C. The contents were cooled to ambient and stirred for 4-5 hours and the product was filtered and washed with toluene and dried under vacuum to obtain finasteride Form I having a purity of about 99.8%.

Example 3

Dichloromethane (150 L) and finasteride (11 kg) were charged to a reactor. Neutral alumina (1 kg) and activated charcoal (1 kg) were added and stirred for 15 minutes at a temperature of 25-35° C. and filtered. The filtrate was transferred to another reactor and dichloromethane was distilled out until a thick slurry was obtained. Isopropyl acetate (80 L) was added and the distillation was continued until the vapour temperature reached about 80° C. The product was filtered hot and washed with isopropyl acetate and dried under vacuum at 80° C. to obtain finasteride Form I having a purity of about 99.8%.

Example 4

Pharmaceutical Formulation

| SI No | Name of Ingredients | Qty/tab (mg) |
|---|---|---|
| | INTRAGRANULAR | |
| 1. | Finasteride USP | 5.00 |
| 2. | Lactose monohydrate | 79.45 |
| 3. | Sodium starch glycolate | 10.00 |
| 4. | Starch | 35.00 |
| | BINDER | |
| 5. | Starch (for spray) | 0.80 |
| 6. | Lactose monohydrate (for spray) | 12.00 |
| 7. | Purified water | q.s. |
| | EXTRAGRANULAR | |
| 8. | Colloidal silicon dioxide | 1.50 |
| 9. | Sodium starch glycolate | 5.00 |
| 10. | Docusate sodium benzoate | 0.50 |
| 11. | Magnesium stearate | 0.75 |
| | Tablet weight | 150.00 |
| | COATING | |
| 12. | Opadry 04F50702 blue | 5.00 |
| 13. | Purified water | q.s. |
| | Total | 155.00 |

Certain modifications and improvements of the disclosed invention will occur to those skilled in the art without departing from the scope of invention, which is limited only by the appended claims.

We claim:

1. A process of preparing finasteride Form I, which process comprises the steps of: (i) dissolving finasteride in a solvent to form a solution; (ii) distilling off the solvent from the solution obtained in step (i); (iii) adding a non solvent to the product of step (ii); and (iv) isolating finasteride Form I.

2. A process according to claim 1, wherein said solvent is methanol or dichloromethane.

3. A process according to claim 1, wherein dissolution of said finasteride in said solvent is carried out at a temperature in the range of ambient to reflux.

4. A process according to claim 1, wherein the solution of the finasteride in the solvent is clarified using decolourising agents.

5. A process according to claim 1, wherein said non solvent is water.

6. A process according to claim 1, wherein said non solvent is an organic solvent in which the solubility of finasteride in not more than about 5% w/v.

7. A process according to claim 6, wherein said organic non solvent is selected from the group consisting of hexane, heptane, octane, toluene, xylene, isobutyl acetate and isopropyl acetate.

8. A process according to claim 1, further comprising stirring a product obtained following step (iii).

* * * * *